United States Patent [19]

Hosoi et al.

[11] Patent Number: 5,867,248
[45] Date of Patent: Feb. 2, 1999

[54] OPTOMETRIC APPARATUS

[75] Inventors: Yoshinobu Hosoi; Hiroshisa Terabe; Akihiro Hayashi, all of Aichi, Japan

[73] Assignee: Nidek Co., Ltd., Aichi, Japan

[21] Appl. No.: 928,660

[22] Filed: Sep. 12, 1997

[30] Foreign Application Priority Data

Sep. 12, 1996 [JP] Japan .................................. 8-265282

[51] Int. Cl.⁶ ................................................ A61B 3/00
[52] U.S. Cl. ........................ 351/200; 351/205; 351/245
[58] Field of Search ................................. 351/200, 205, 351/245, 246

[56] References Cited

U.S. PATENT DOCUMENTS

| | | | |
|---|---|---|---|
| 5,416,540 | 5/1995 | Hayashi ................................. | 351/239 |
| 5,444,504 | 8/1995 | Kobayashi et al. .................... | 351/237 |
| 5,610,671 | 3/1997 | Hosoi et al. .......................... | 351/200 |
| 5,627,612 | 5/1997 | Hayashi ............................... | 351/200 |
| 5,767,940 | 6/1998 | Hayashi et al. ....................... | 351/205 |

*Primary Examiner*—Huy Mai
*Attorney, Agent, or Firm*—Sughrue, Mion, Zinn, Macpeak & Seas, PLLC

[57] ABSTRACT

An optometric apparatus designed to ensure that measurement results can be readily confirmed before they are printed out, and to prevent the deletion of data due to an erroneous operation of a switch. The optometric apparatus having examining device for examining the visual function of an eye to be examined, comprising: memory for storing data on examination by the examining device; display device having a display screen for displaying the examination data; printing device for printing the examination data stored in the memory; a print switch for inputting a signal for printing the examination data to the printing device; display control circuit for displaying the examination data on the display device on the basis of the signal from the print switch; confirmation-signal generating switch for generating a confirmation signal for confirming the absence of an abnormality in the examination data; and commanding circuit for commanding the printing device to effect printing on the basis of the confirmation signal.

7 Claims, 15 Drawing Sheets

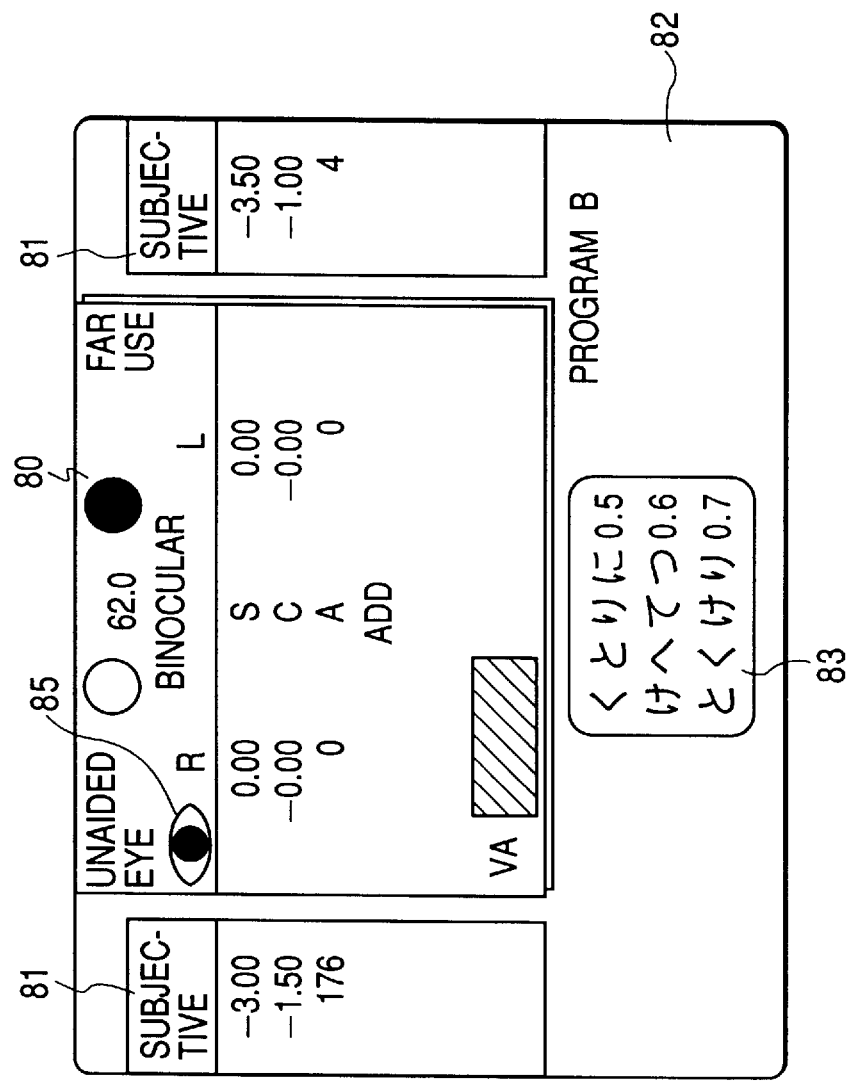

FIG. 15

TABLE A (POWER ADJUSTMENT FOR MYOPIA [INITIAL WEARING])

| PERFECT CORRECTION S1 | CORRECTION AMOUNT ΔS1 |
|---|---|
| −0.25<br>−0.50<br>−0.75<br>−1.00<br>−1.25<br>−1.50<br>−1.75<br>−2.00<br>−2.25<br>−2.50<br>−2.75<br>−3.00<br>−3.25<br>−3.50<br>−3.75<br>−4.00<br>−4.25<br>−4.50<br>−4.75<br>−5.00<br>⋮ | S1/2<br>(HOWEVER, ROUNDED UP IN 0.25D STEPS) |

TABLE B (POWER ADJUSTMENT FOR MYOPIA [2ND TIME OR MORE])

| DIFFERENCE BETWEEN FORMER SPECTACLES AND PERFECT CORRECTION S2 | CORRECTION AMOUNT ΔS2 |
|---|---|
| ⋮<br>+0.50<br>+0.25<br>0 | } 0 |
| −0.25<br>−0.50<br>−0.75<br>−1.00<br>−1.25<br>−1.50<br>−1.75 | S2/2<br>(HOWEVER, ROUNDED UP IN 0.25D STEPS) |
| −2.00<br>−2.25<br>−2.50<br>−2.75<br>−3.00<br>⋮ | } S2+0.75 |

TABLE C (POWER ADJUSTMENT FOR ASTIGMATISM [INITIAL WEARING])

| PERFECT CORRECTION C1 | CORRECTION AMOUNT ΔC1 |
|---|---|
| −0.25<br>−0.50<br>−0.75<br>−1.00<br>−1.25<br>−1.50<br>−1.75<br>−2.00<br>−2.25<br>−2.50<br>−2.75<br>−3.00<br>−3.25<br>−3.50<br>−3.75<br>⋮ | C1/2<br>(HOWEVER, ROUNDED UP IN 0.25D STEPS) |

TABLE D (POWER ADJUSTMENT FOR ASTIGMATISM [2ND TIME OR MORE])

| DIFFERENCE BETWEEN FORMER SPECTACLES AND PERFECT CORRECTION C2 | CORRECTION AMOUNT ΔC2 |
|---|---|
| ⋮<br>+0.50<br>+0.25<br>0 | } 0 |
| −0.25<br>−0.50<br>−0.75<br>−1.00<br>−1.25<br>−1.50<br>−1.75 | C2/2<br>(HOWEVER, ROUNDED UP IN 0.25D STEPS) |
| −2.00<br>−2.25<br>−2.50<br>−2.75<br>−3.00<br>−3.25<br>⋮ | } C2+0.75 |

OPTOMETRIC APPARATUS

BACKGROUND OF THE INVENTION

The present invention relates to an optometric apparatus for examining the visual function of an eye to be examined.

In an examination for prescribing spectacle lenses or the like for correcting a refractive error which is present in an eye to be examined, an optometric apparatus is used for subjectively examining the refractive power of the eye to be examined, and after obtaining a perfect correction power, the perfect correction power is adjusted to determine a prescription power. In conducting the subjective examination, preliminary tests including an objective test, measurement of former spectacle values, an unaided visual acuity test, a visual acuity test based on the former spectacle, and the like are performed, and these data are inputted to the apparatus.

Upon completion of all the tests, a print switch of the apparatus is pressed to print out the inputted data and the test results from a printer. When this printout is finished, the apparatus is initialized to return to its initial state. The paper on which the data on the test results have been printed is attached to a clinical chart or the like, and is used for the management of the subject's data. In addition, when the data inputted to the apparatus or the test results are not necessary, or when the measurement results are directly written in the clinical chart or the like, a data deleting switch provided on the apparatus may be pressed to delete the stored data.

However, it is not uncommon to find an omission in measurement and an abnormality in the data upon looking at the results on the printout or the results transcribed onto the clinical chart. In such a case, the examination is conducted again, but after the printout or deletion of the data, the optical systems must be set again and the data must be inputted again, which is quite troublesome. Furthermore, if the data deleting switch or the like is erroneously operated, the data is unintentionally deleted.

SUMMARY OF THE INVENTION

In view of the above-described drawbacks of the conventional art, an object of the present invention is to provide an optometric apparatus which makes it possible to readily confirm measurement results before they are printed out, and to prevent the deletion of data due to an erroneous operation of a switch.

To overcome the above-described drawbacks, the present invention is characterized by the following features.

(1) An optometric apparatus having examining means for examining the visual function of an eye to be examined, comprising: storing means for storing data on examination by the examining means; display means having a display screen for displaying the examination data; printing means for printing the examination data stored in the storing means; a print switch for inputting a signal for printing the examination data to the printing means; display control means for displaying the examination data on the display means on the basis of the signal from the print switch; confirmation-signal generating means for generating a confirmation signal for confirming the absence of an abnormality in the examination data; and commanding means for commanding the printing means to effect printing on the basis of the confirmation signal.

(2) In the optometric apparatus according to (1), the print switch is jointly used as the confirmation-signal generating means.

(3) The optometric apparatus according to (1) further comprises: examination-data deleting means for deleting the examination data on the basis of a print command signal from the commanding means.

(4) The optometric apparatus according to (1) further comprises: an examination-data deletion switch for generating a signal for deleting the examination data; second display control means for displaying the examination data on the display means on the basis of the signal from the examination-data deletion switch; second confirmation-signal generating means for generating a confirmation signal for confirming the absence of an abnormality in the examination data; and executing means for executing the deletion of the examination data on the basis of the confirmation signal.

(5) In the optometric apparatus according to (4), the examination-data deletion switch is jointly used as the second confirmation-signal generating means.

(6) The optometric apparatus according to any one of (1) to (5) further comprises: returning means for returning to a state of examination by the examining means.

As one of advantages of the present invention, the measurement results can be readily confirmed before they are printed out, and the deletion of data due to an erroneous operation of the switch can be prevented.

BRIEF DESCRIPTION OF THE DRAWINGS

In the accompanying drawings:

FIG. 7 is a diagram illustrating an example of the measurement screen displayed on a display;

FIG. 15 is a diagram illustrating tables for obtaining correction amounts for adjusting correction powers.

DETAILED DESCRIPTION OF THE PREFERRED EMBODIMENT

Figure 1:
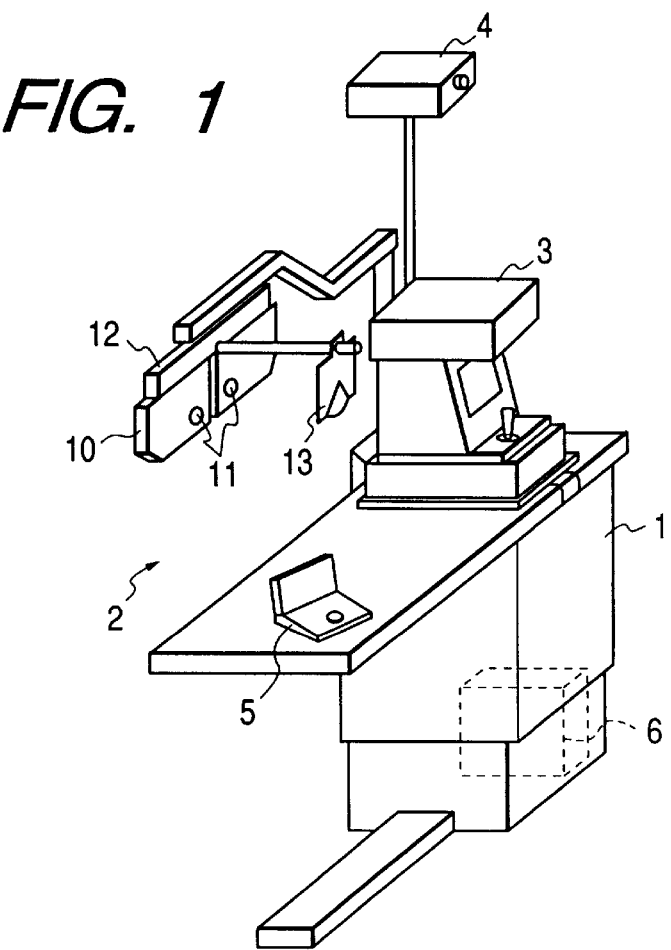
FIG. 1 is an external view illustrating an overall configuration of an optometric apparatus in accordance with an embodiment.

Referring now to the drawings, a description will be given of an embodiment of the present invention. FIG. 1 is an external view illustrating an overall configuration of an optometric apparatus in accordance with the embodiment. Reference numeral 1 denotes an examination table disposed between a subject and an examiner, and reference numeral 2 denotes a subjective-type refractive-power measuring device 2. The subjective-type refractive-power measuring device 2 is provided with a pair of left and right lens units 10 in which various optical elements are electrically driven so as to be selectively disposed in a pair of test windows 11. Numeral 3 denotes an objective-type ocular refractive-power measuring device for measuring the refractive power of the eye by projecting a measuring index onto the eyeground of the subject eye and detecting a projected image of the index on the eyeground by means of a light receiving means. The objective-type ocular refractive-power measuring device 3 has the function of obtaining the interpupillary distance on the basis of an amount of movement of its measuring section having a measuring optical system when the measuring section is moved from a state of completion of alignment of one eye to a state of completion of alignment of the other eye. The objective-type ocular refractive-power measuring device 3 is placed on a moving tray which is slidable on the examination table 1, and during an objective examination the objective-type ocular refractive-power measuring device 3 is slid to a central position on the examination table 1 to execute measurement.

Figure 2:
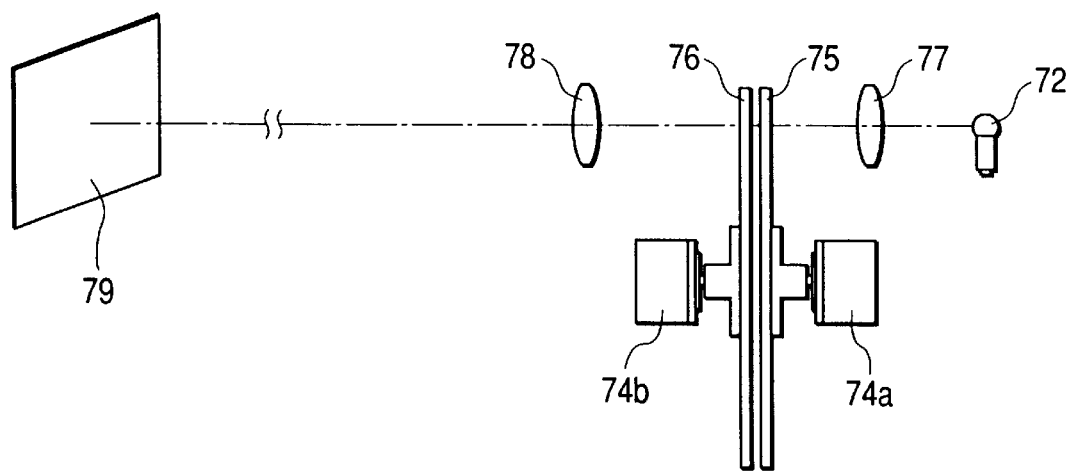
FIG. 2 is a diagram illustrating a schematic configuration of an optical system of a target presenting device.

Numeral 4 denotes a projection-type target presenting device for presenting various test targets. As shown in FIG. 2, the projection-type target presenting device 4 is provided with a lamp 72, a focusing lens 77, a target disk 75 with test targets depicted on the same circumference, a motor 74a for rotating the target disk 75, a mask disk 76 for masking the target, a motor 74b for rotating the mask disk 76, and a projection lens 78. The bundle of rays emitted from the lamp 72 is focused by the focusing lens 77, and illuminates the target on the target disk 75 and the mask disk 76. The target bundle of rays which has passed through the mask disk 76 is projected onto a projection screen 79 disposed forwardly of the projection lens 78.

Numeral 5 denotes a controller for operating the subjective-type refractive-power measuring device 2 and the target presenting device 4, and numeral 6 denotes a relay unit for relaying communication between the respective devices. An unillustrated lens meter is connected to the relay unit 6.

Figure 3:
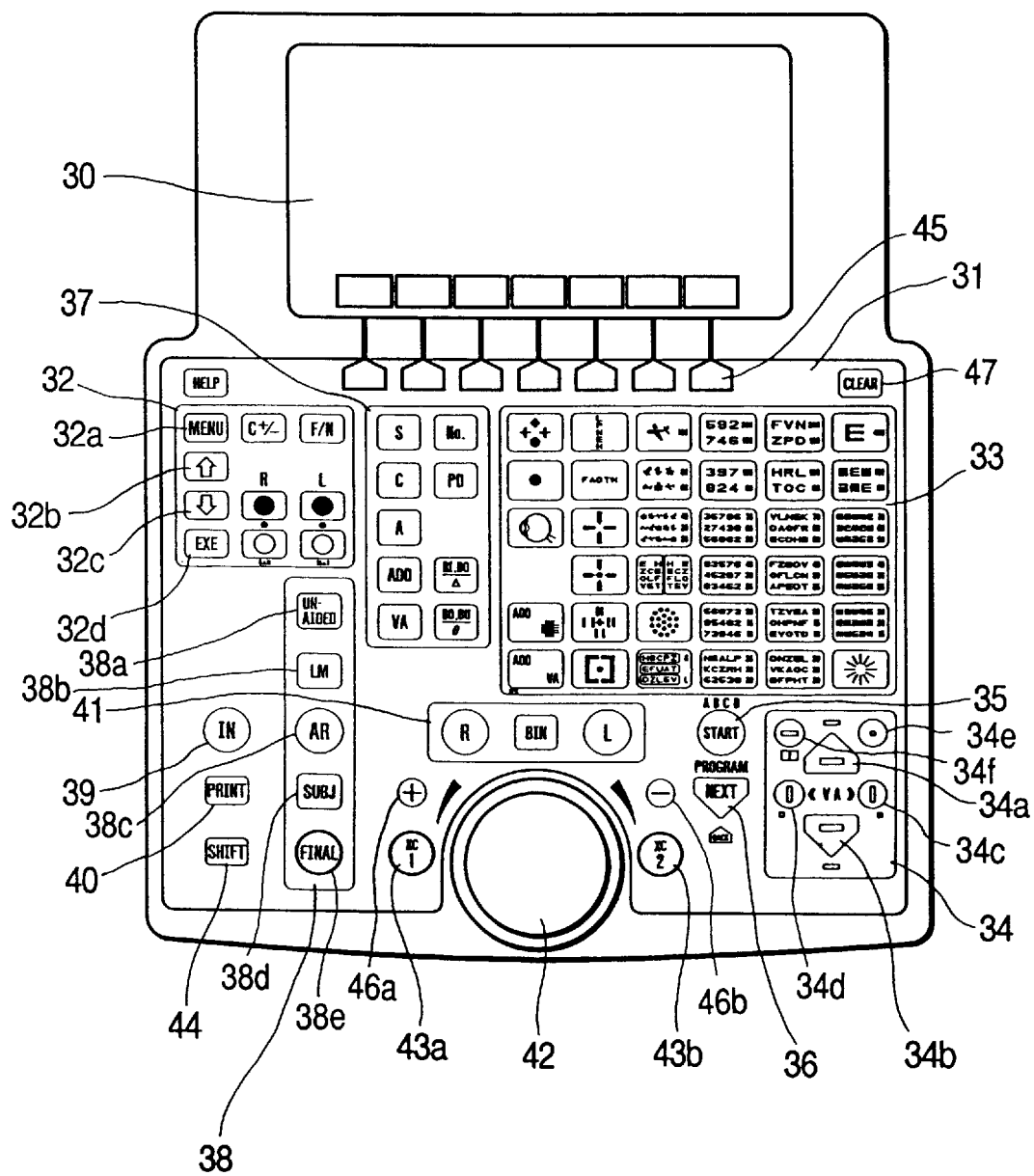
FIG. 3 is a top view of a controller 5.

FIG. 3 is a top view of the controller 5. Reference numeral 30 denotes a liquid-crystal display which displays optimetric information. Numeral 31 denotes a switch section which is provided with the following switches: a group of setting changeover switches 32 having switches which are used when changing over a display screen to a menu screen of the display 30 and effecting such as the setting of parameters; a group of target switches 33 for changing over a test target to be presented from the target presenting device 4; a group of mask switches 34 for applying a mask necessary for the visual acuity test target (chart). The following switches are provided as the group of mask switches 34: a horizontal mask switch 34a for applying a horizontal mask over an upper stage of the visual acuity test target (chart); a horizontal mask switch 34b for applying a horizontal mask over a lower stage; a switch 34c for applying a vertical mask over the right-hand side of the visual acuity test target (chart); a switch 34d for applying a vertical mask over the left-hand side; a one-character mask switch 34e for applying a one-character mask (when this switch is used alone, a one-character mask is applied over an upper right corner); and a switch 34f for applying a horizontal mask over a middle stage of the visual acuity test target (chart). In addition, the switches 34a, 34b, 34c, and 34d also serve as switches for moving the masking position toward an upper side, a lower side, a right side, and a left side, respectively.

The switch section 31 further includes the following switches: a start switch 35 for executing programmed optometry; an advance switch 36 for advancing the item of programmed optometry to an ensuing item; a group of item designating switches 37 for designating an item of such as measurement data to be changed; a group of measurement-mode designating switches 38 for designating a mode for entering data or a mode for measurement; a data input switch 39 which is used when inputting data from the objective-type ocular refractive-power measuring device, the lens meter, and the like; a print switch 40; a measurement-eye designating switch 41; and a dial switch 42 which is used when changing measurement values and inputting numerical values. Numerals 46a and 46b respectively denote a "+" switch and a "−" switch which are used for increasing or decreasing numerical values that are inputted.

Reference numerals 43a and 43b denote changeover switches for changing over a cross-cylinder, and these changeover switches 43a and 43b are also used during adjustment of appearances in the stage of prescription. Numeral 44 denotes a shift switch, and if another switch is pressed while this switch is being pressed, it is possible to provide a function which is different from the function with which that switch is generally provided (a description thereof will be given later). Numeral 45 denotes a group of function switches which are used when selecting switches corresponding to switch displays which are displayed at predetermined positions in a lower portion of the screen of the display 30. Numeral 47 denotes a clear switch which is used when deleting data inputted to the controller 5.

Figure 4:
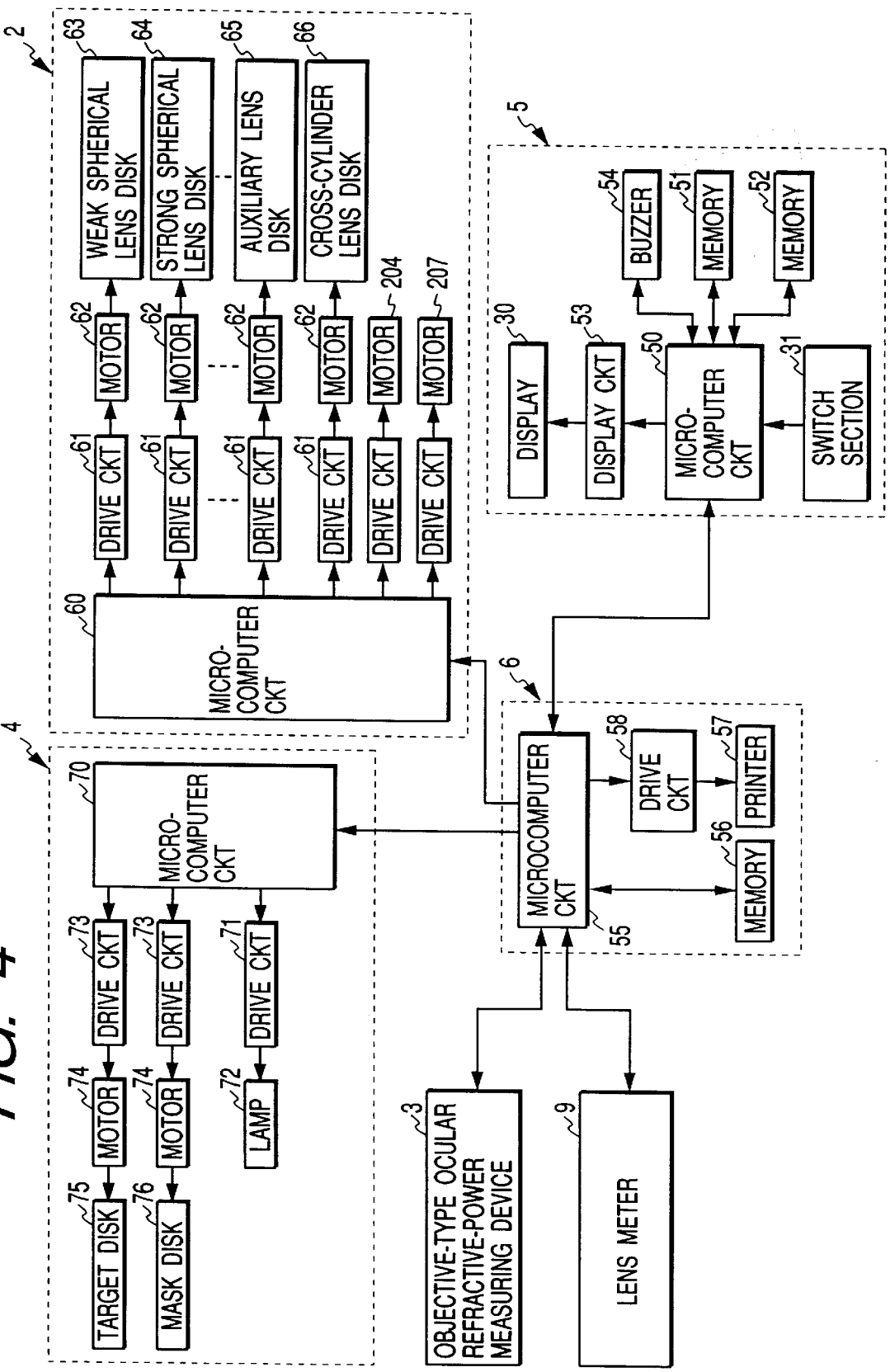
FIG. 4 is a block diagram illustrating the control of the apparatus in accordance with the embodiment.

FIG. 4 is a block diagram for describing the control of the apparatus. A switch signal from the switch section 31 of the controller 5 is subjected to predetermined processing, and is then inputted to a microcomputer circuit 50. Connected to the microcomputer circuit 50 are a memory 51 for storing a control program such as an optometric program, as well as a memory 52 for storing objective value data and the like. The microcomputer circuit 50 converts the switch signal to various data on the basis of the control program stored in the memory 51, and controls the screen of the display 30 through a display circuit 53. In addition, the converted signal is inputted to a microcomputer circuit 55 of the relay unit 6. The microcomputer circuit 55 supplies data on refractive power and the movement of lens units 10 to the subjective-type refractive-power measuring device 2 and supplies data on the target to the target presenting device 4.

A microcomputer circuit 60 of the subjective-type refractive-power measuring device 2 which has received the data on the refractive power drives motors 62 via drive circuits 61 to rotate a weak spherical disk 63, a strong spherical disk 64, an auxiliary lens disk 65, a cross-cylinder disk 66, and the like, thereby disposing predetermined optical systems in the test windows 11. A multiplicity of optical elements having various optical characteristics are disposed on the same circumference of each lens disk, and corrective optical systems are formed by a combination thereof. In addition, the microcomputer circuit 60, upon receiving signals concerning the sliding and flapping of the lens units 10, drives the drive motors 204 and 207.

A microcomputer circuit 70 of the target presenting device 4 which has received the data on the target lights up the lamp 72 via a drive circuit 71, drives two motors 74a and 74b via two drive circuits 73, and rotates the target disk 75 with a target depicted thereon and the mask disk 76, respectively, thereby projecting a predetermined test target onto an unillustrated screen placed in front of the eye being examined.

The objective-type ocular refractive-power measuring device 3 and a lens meter 9 are connected to the microcomputer circuit 55, and measurement data sent to the microcomputer circuit 55 is stored in a memory 56. When a read command signal is inputted from the microcomputer circuit 50 on the controller 5 side to the microcomputer circuit 55, the microcomputer circuit 55 reads the designated measurement data from the memory 56 and transfers the same to the controller 5. Numeral 57 denotes a printer for outputting the results of measurement, and 58 denotes a drive circuit thereof.

Figure 5:
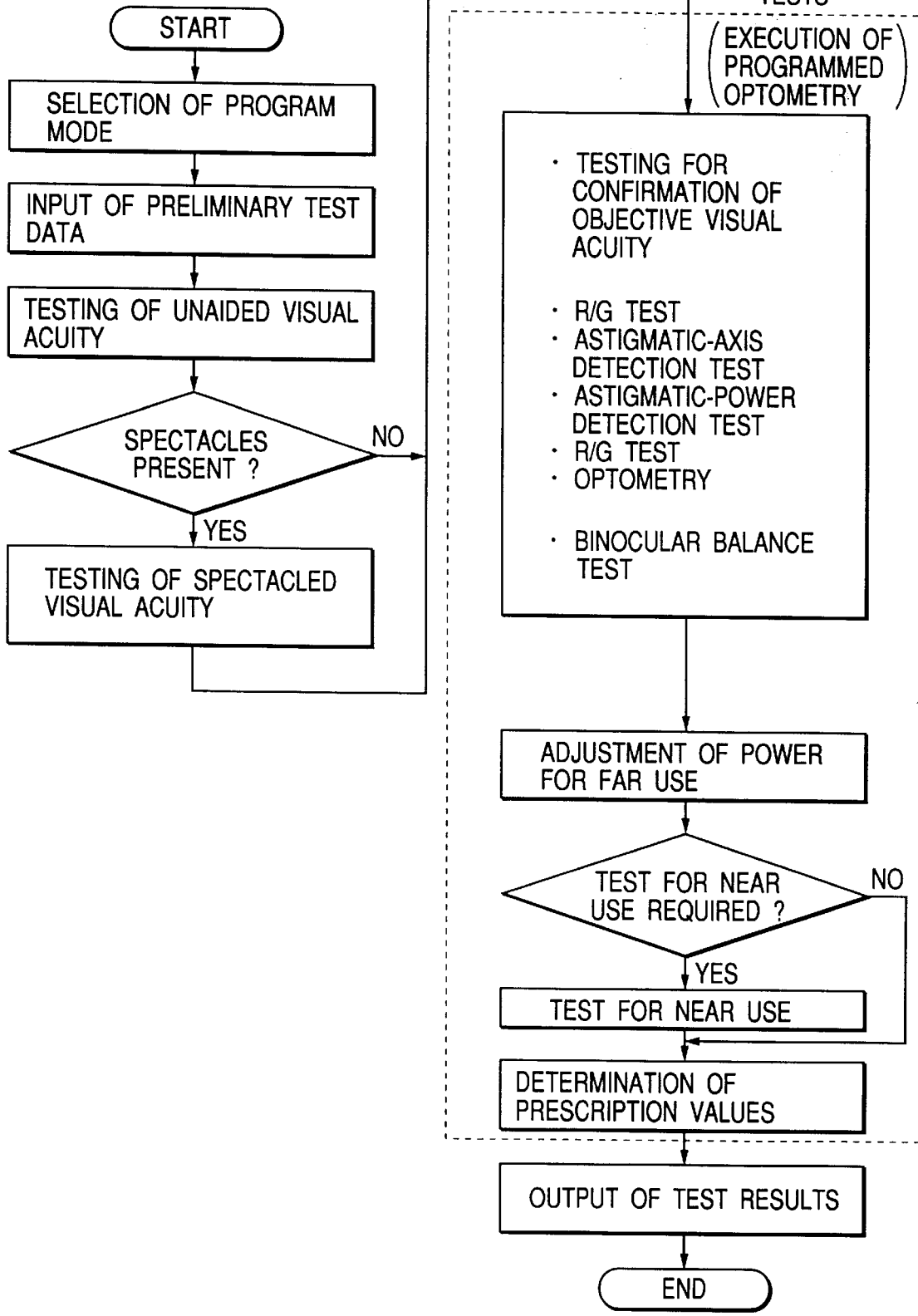
FIG. 5 is a flowchart illustrating an examination procedure in a case where an optometric program B for simplified examination provided in the apparatus of the embodiment is selected.

A description will be given of the operation of the apparatus having the above-described configuration. In the apparatus of the embodiment, a plurality of optometric programs, for which examination items and examination procedures have been set in advance, are stored in the memory 51, and the examiner is able to select a mode of the optometric program in accordance with his or her policy of examination. As the optometric program modes, a program A for standard examination and a program B for simplified examination have been prepared, and a program C and a program D written and inputted by the examiner himself or herself can be further prepared. The names of the modes of the programs which can be executed by the start switch 35 are displayed on the initial screen of the display 30. As to which of the optometric programs is to be used to effect examination, the modes (A, B, C, and D) of the optometric programs can be consecutively changed over by pressing the start switch 35 while pressing the shift switch 44. Hereafter, a description will be given of an example in which the optometric program B for simplified examination provided in this apparatus is selected (see FIG. 5).

<Selection of Program Mode>

In examination, after effecting necessary input processing such as the setting of parameters, the name of the program modes displayed on the initial screen for measurement of the display 30 are confirmed, and the program B is selected by means of the shift switch 44 and the start switch 35.

<Input of Preliminary Test Data>

(a) Input of Objective Value Data and Spectacle Value Data

Objective value data such as S (power of the spherical lens (spherical power)), C (power of astigmatism (cylinder power)), A (angle of astigmatic axis (cylinder axis)), and the like, which are obtained from the objective-type ocular refractive-power measuring device 3, are automatically transferred to and stored in an objective value memory area of the memory 52 on the controller 5 side by pressing an objective switch 38c of the group of switches 38 after pressing the data input switch 39. In addition, in the case where the lens meter 9 is connected, such objective value data are similarly transferred to and stored in a spectacle value memory area of the memory 52 by pressing a spectacle switch 38b of the group of switches after pressing the data input switch 39. Further, the objective value data stored in the objective value memory area are concurrently stored in a subjective value memory area as well. The reason for this is that it is the general practice to adopt an examination method in which optical systems which are initially set in the test windows 11 of the lens units 10 are made to correspond to the objective value data (as to which of the optical systems corresponding to the objective value data or the optical systems corresponding to the spectacle value data is to be initially set, selection can be made in advance by the setting of parameters).

It should be noted that in cases where the objective-type ocular refractive-power measuring device 3 and the lens meter 9 are not connected, manual input can be made in the following procedure: First, the type of objective value data or spectacle value data to be inputted is selected by pressing the objective switch 38c or the spectacle switch 38b, and the input switch 39 is pressed. The screen of the display 30 is thus changed over to the selected screen for inputting objective values or spectacle values. Next, after a measurement item such as S, C, A, or ADD (addition power) is designated, R (right eye), L (left eye), or both eyes is designated by the measurement-eye designating switch 41. On the display 30, a numerical-value input portion for the designated measurement item and a numerical-value input portion for the designated eye are inversely displayed, allowing an input to be made. A numerical value is inputted by rotating the dial switch 42. At this time, in this apparatus, with respect to the adjustment step of the numerical value when the dial switch 42 is used singly, an input can be made with the range of the adjustment step made variable if the dial switch 42 is used while the shift switch 44 is being pressed. The range of the adjustment step which is changed by the dial switch 42 is selected and set in advance by the parameter setting for each item.

Figure 6:
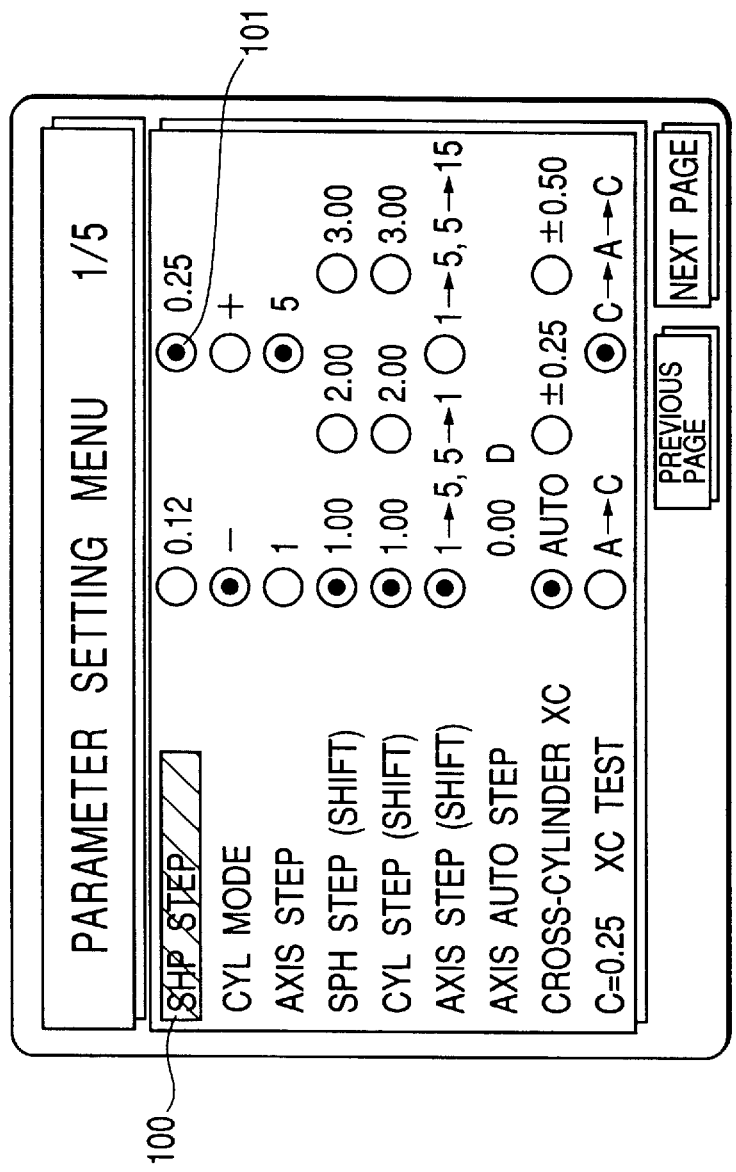
FIG. 6 is a diagram illustrating an example of the screen for setting, various parameters.

The parameter setting for determining the range of the adjustment step is effected as follows. If a parameter setting menu is selected from among the items of selection in the set menu, a screen for setting various parameters is displayed on the display 30, as shown in FIG. 6. The setting can be changed for the item where a cursor 100 being inversely displayed is located, so that the cursor being inversely displayed is moved to the item requiring a change by using move switches 32b and 32c of the group of switches 32. In the case where the dial switch 42 is used singly to enter numerical values, 0.12D and 0.25D can be selected as the steps for the S value, and 1 power and 5 powers can be selected as the steps for the A value (incidentally, since the step for the C value is normally 0.25D, this value is adopted in the apparatus of the embodiment, and in the parameter setting a mode for adopting a minus reading or a mode for adopting a plus reading is selected). In the case where the dial switch 42 is used while pressing the shift switch 44, 1.00D, 2.00D, and 3.00D can be selected as the steps for the S value and the C value, respectively. The step for the A value when the shift switch 44 is jointly used is 5 powers when the normal (independent) adjustment step is set to 1 power; however, when the normal adjustment step is set to 5 powers, it is possible to select two modes for changing 5 powers to 1 power and 5 powers to 15 powers. Incidentally, in FIG. 6, a filled-circle mark 101 in each item shows the selected content, and the filled-circle mark 101 can be changed by the dial switch 42.

In the input of numerical values by means of the dial switch 42, it is possible to enter numerical values with different ranges of steps in correspondence with the respective items of correction selectively in the case where the dial switch 42 is used singly and in the case where it is used while pressing the shift switch 44. Therefore, it is possible to efficiently enter large values and readily make fine adjustment.

Upon completion of the input of all the measurement items of objective value data (or spectacle value data), the input switch 39 is pressed again. By means of the signal of this input switch, optical systems which are used when all the inputs are completed are set in the left and right test windows 11 of the subjective-type refractive-power measuring device 2. Since the optical systems which are disposed in the test windows 11 of the lens units 10 are thus set at one time by being changed over to optical systems corresponding to the values entered in the data input (hereafter, this input will be referred to numerical value input according to a preset mode), the changeover of optical systems can be effected without imparting an uneasy sensation or discomfort to the subject when the operation is performed with the lens units 10 disposed in front of the subject's eyes.

(b) Input of Master Eye Data

The examiner conducts an examination for detecting the master eye (dominant eye), as necessary, and enters the result to the apparatus. The detection of the dominant eye can be effected by the punched card method, the Rosenbach method, or the like. The input is made by pressing the R switch or L switch of the measurement-eye designating switch 41 while pressing the shift switch 44. For instance, if it is assumed that R (right eye) is designated, as shown in FIG. 7, a mark 85 meaning that it is the master eye (dominant eye) is displayed on the measurement screen of the display 30 alongside the character "R" indicating the data for the right eye. Thereafter, since this master eye information is always displayed on the measurement screen, the examiner is able to instantly make a determination when a decision is required concerning such as on which of the left and right eyes the priority is to be placed in the binocular balance test, the test for determination of prescription powers, and the like.

In addition, after the master eye data is inputted, when the test result is printed out from the printer 57 after completion of the test, master eye data is printed on the printing paper as "Master Eye: R."

<Testing of Unaided Visual Acuity>

Upon completion of the input of data, an unaided visual acuity test is conducted. If an unaided visual acuity switch 38a of the group of measurement-mode designating switches 38 is pressed, the mode is set in the mode for measuring the unaided visual acuity, and the eye to be measured is designated by means of the R switch or the L switch of the measurement-eye designating switch 41. In this case, since the test window on the measurement eye side of the subjective-type refractive-power measuring device 2 is opened, and the test window on the other eye side is covered, the test can be conducted by disposing the subjective-type refractive-power measuring device 2 in front of the subject's eye. The test may be conducted by causing the subject to hold an eye cover.

As a result of the designation of the eye to be measured, the VA column of a central display portion 80 displayed on the display 30 assumes a state in which a visual acuity value of the designated side can be inputted (see FIG. 7). The examiner makes a rough estimate of the subject's unaided visual acuity value on the basis of the objective value data or the like, and selects a visual acuity test target (chart) having that visual acuity value among the group of target switches 33. The selected target (chart) is presented from the target presenting device 4, and a target pattern 83 being currently presented is displayed in an operation explanation area 82 below the central display portion 80 of the display 30.

A description will be given of the visual acuity test. When conducting the visual acuity test, a method is generally adopted in which a one-character mask or a vertical mask is applied over the visual acuity test target (chart) being presented, the subject is then made to read the target starting from a character of a smaller visual acuity value toward a character of a larger visual acuity value, and the test proceeds in the horizontal direction when the character is illegible. In this case, when the presented target characters in the upper stage are illegible, the test target (chart) is changed over to one having a group of target characters of smaller visual acuity values. Meanwhile, when the presented target characters in the lower stage are legible, the test target (chart) is changed over to one having a group of target characters of larger visual acuity values. Then, depending on the stage where the target has ceased to be legible among the upper stage, the middle stage, and the lower stage of the presented target, the test is performed by changing over the position where the horizontal mask or the one-character mask is applied. At this time, this apparatus can be easily set in a desired masked state by reducing the number of operations by means of a limited number of switches provided in the group of mask switches 34 as well as the shift switch 44.

Figure 8A:
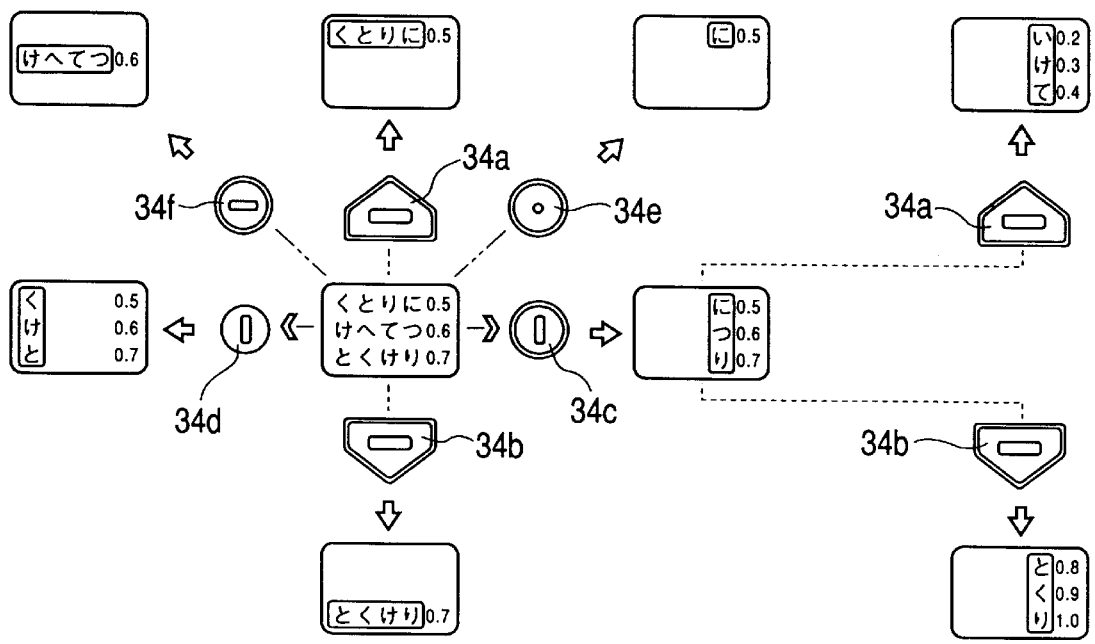
FIG. 8a is a diagram illustrating a masking operation by the independent operation of a group of mask switches.
Figure 8B:
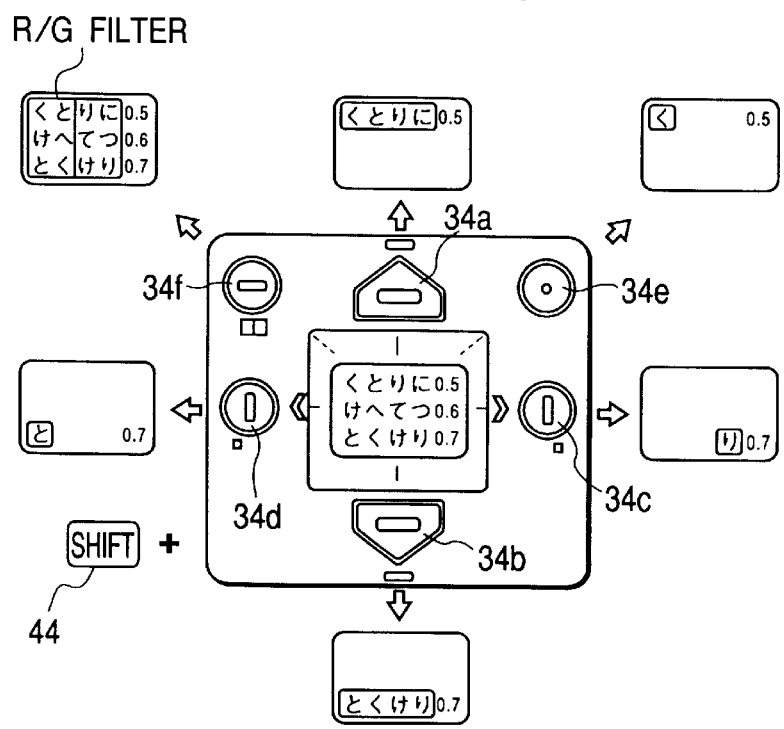
FIG. 8b is a diagram illustrating a masking operation in a case where the group of mask switches is operated while pressing a shift switch.
Figure 9:
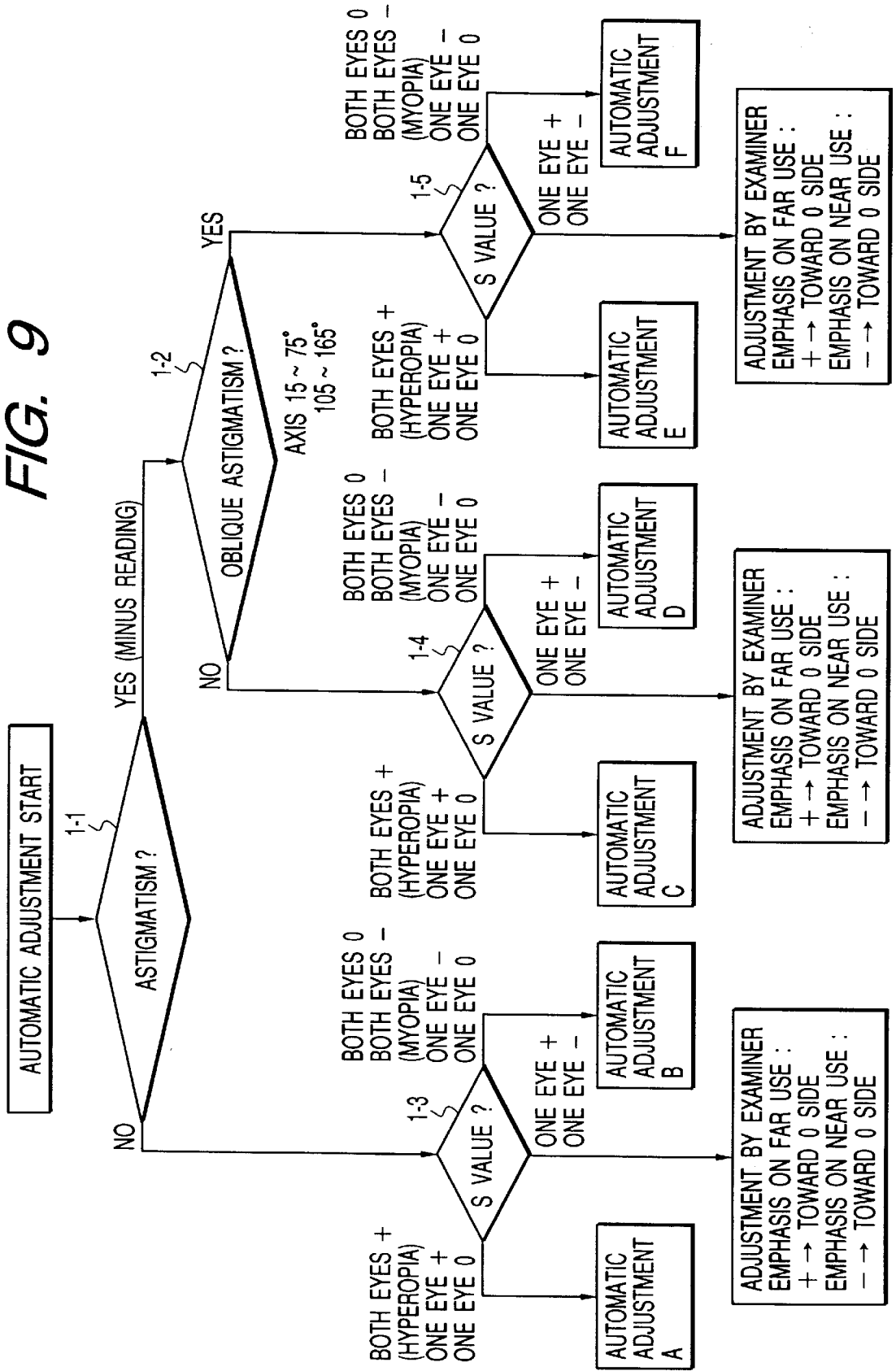
FIG. 9 is a diagram illustrating a flowchart of an automatic adjustment program for estimating prescription powers.
Figure 10:
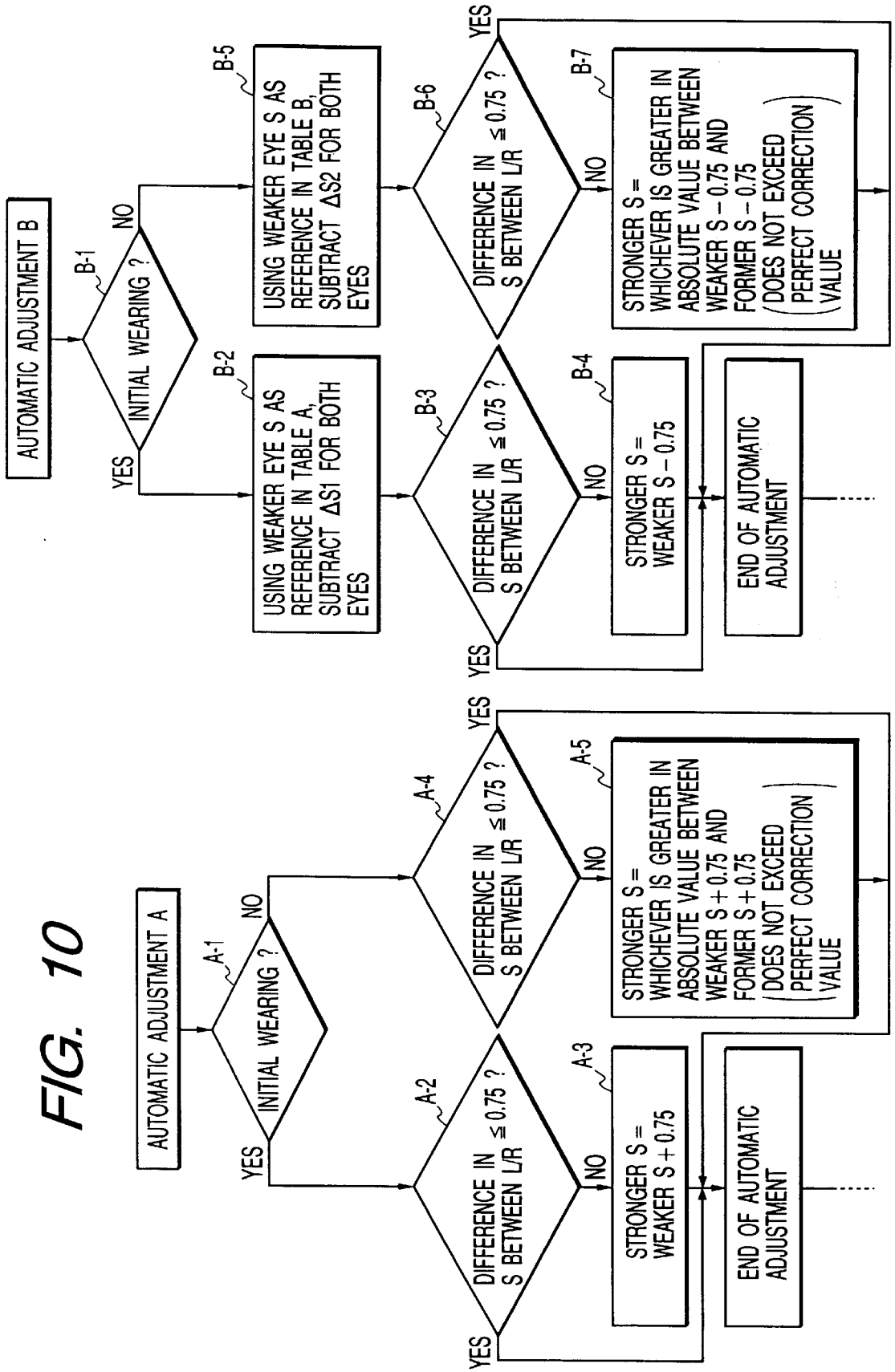
FIG. 10 is a diagram illustrating flowcharts of automatic adjustment programs for estimating prescription powers.
Figure 11:
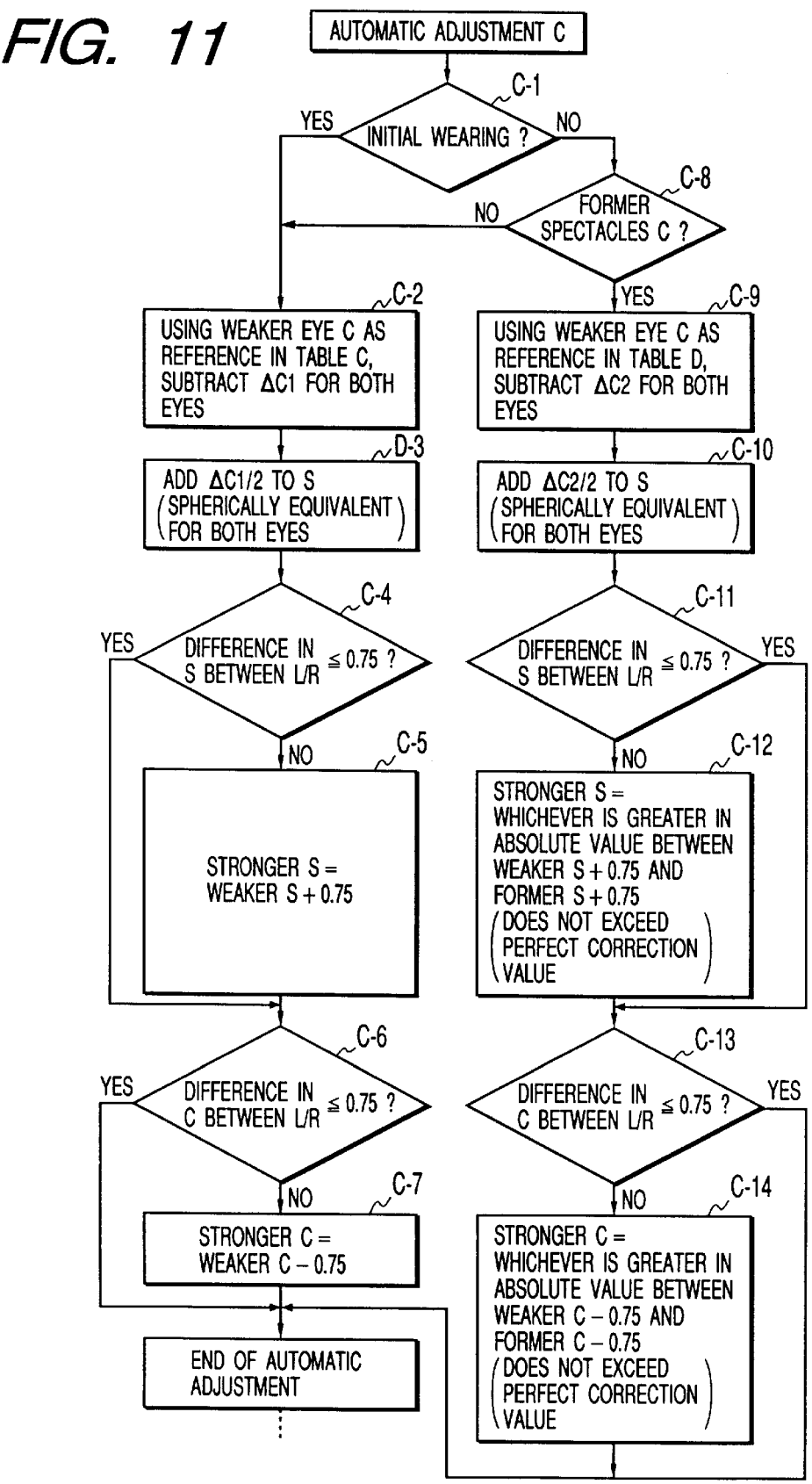
FIG. 11 is a diagram illustrating a flowchart of an automatic adjustment program for estimating prescription powers.
Figure 12:
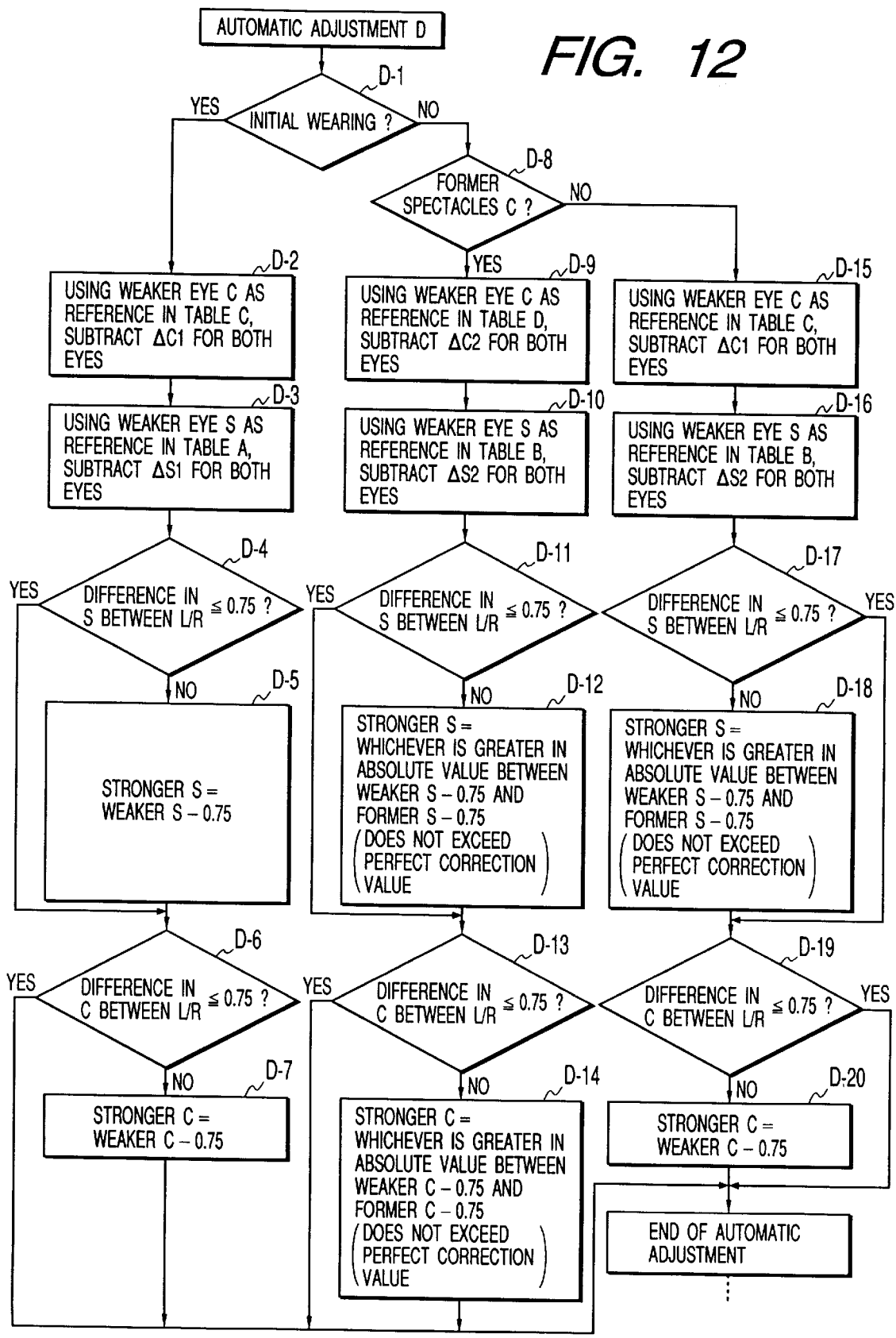
FIG. 12 is a diagram illustrating a flowchart of an automatic adjustment program for estimating prescription powers.
Figure 13:
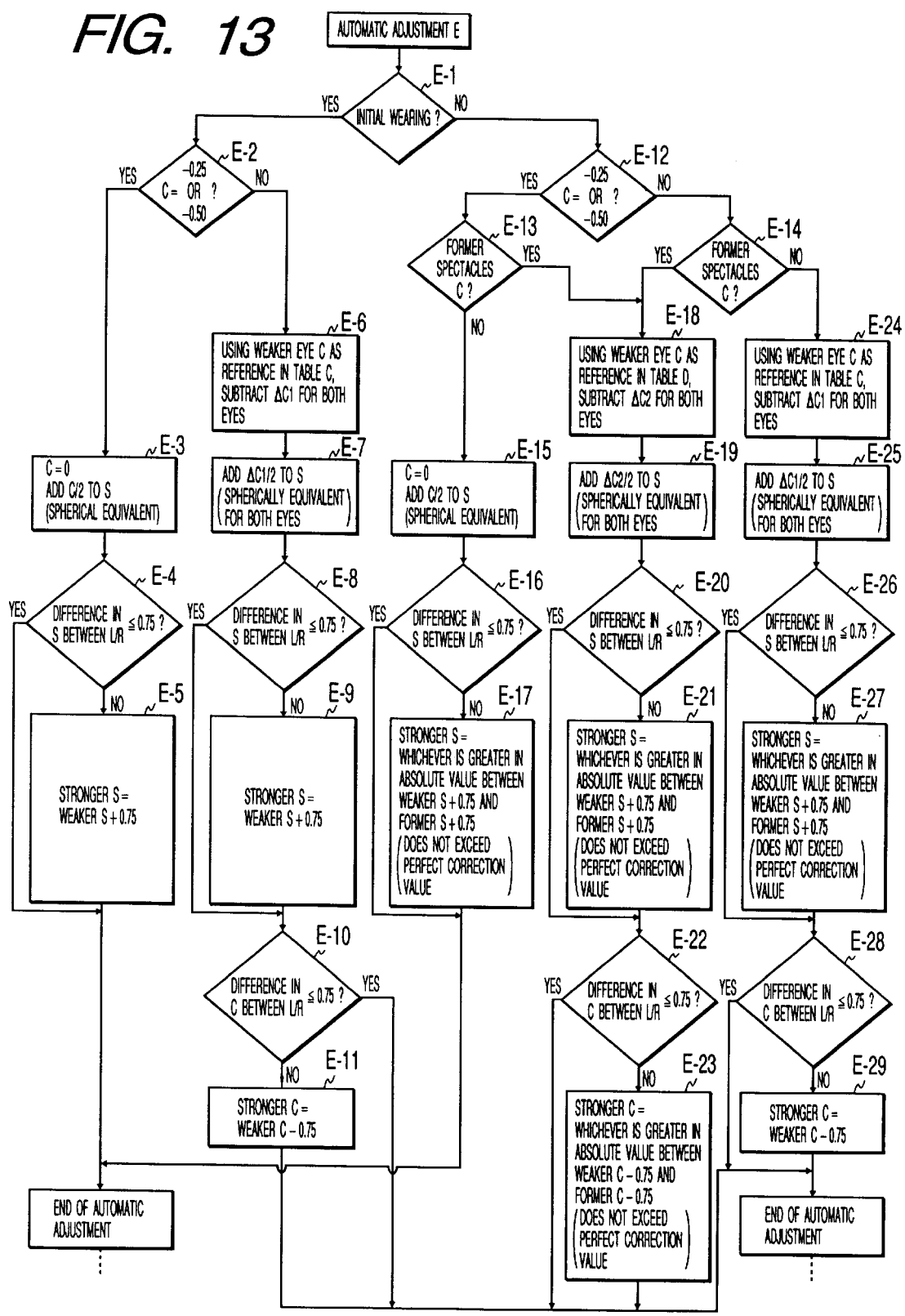
FIG. 13 is a diagram illustrating a flowchart of an automatic adjustment program for estimating prescription powers.
Figure 14:
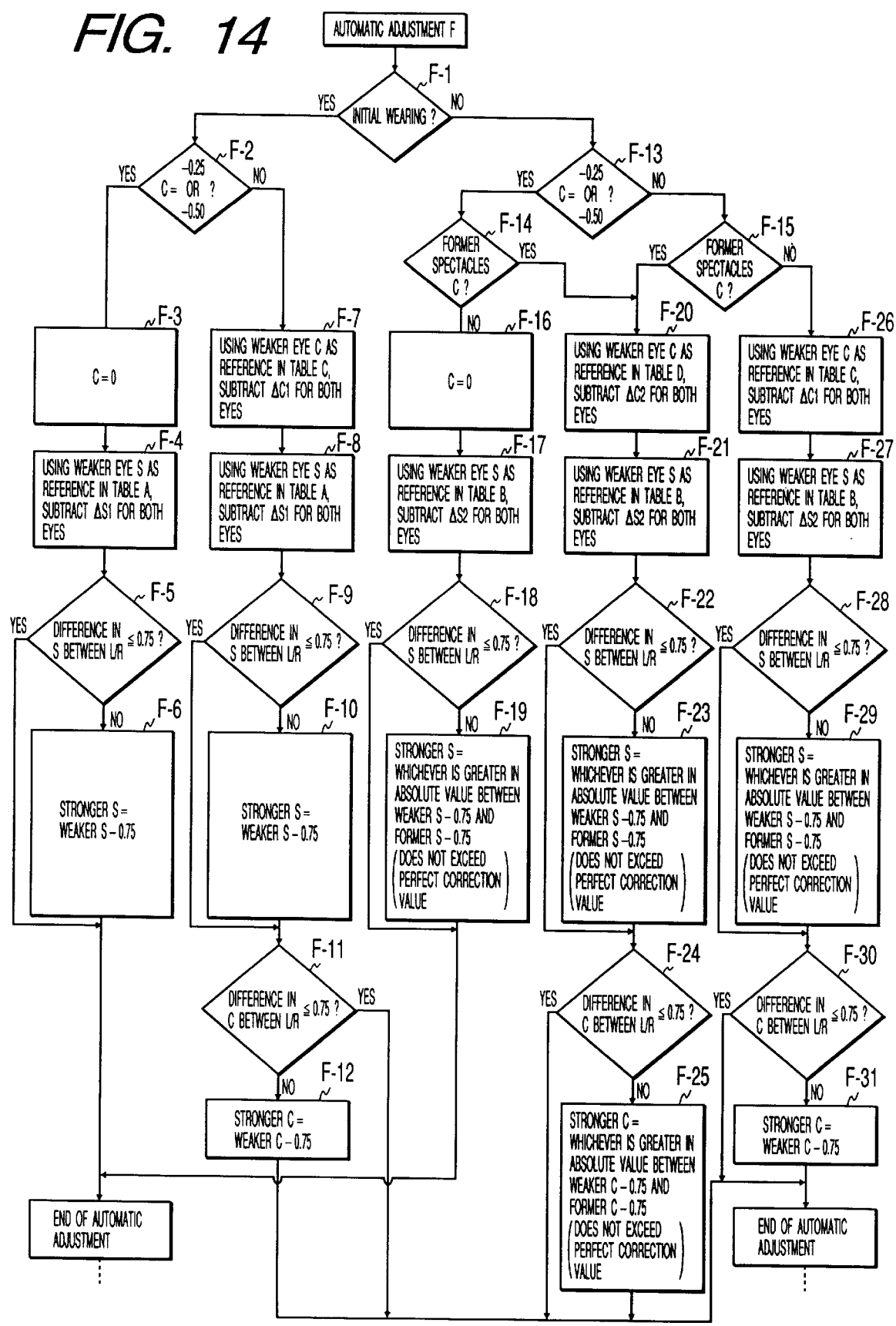
FIG. 14 is a diagram illustrating a flowchart of an automatic adjustment program for estimating prescription powers.

Referring to FIG. 8, a description will be given of the masking operation. FIG. 8(a) is a diagram explaining the independent operation of the group of mask switches 34 without using the shift switch 44. FIG. 8(b) is a diagram explaining the operation while pressing the shift switch 44. First, a description will be given of the case in which the test is performed by using the vertical mask. For instance, the switch 34c is first pressed to apply the vertical mask so that only the target column at the right-hand end is presented, and the subject is made to read that column starting from the upper stage. If the stage where the target has ceased to be legible is the middle stage, the horizontal mask can be applied over the middle stage by means of the switch 34f. If the stage where the target has ceased to be legible is the upper stage (or the lower stage), the following procedure is taken. If the operation is effected singly by using the group of mask switches 34, the visual acuity test target (chart) is selected again among the group of target switches 33 to cancel the masking, and the switch 34a or 34b is pressed again to apply the horizontal mask (the same also applies to the case of the one-character mask). According to this procedure, not only does it take time in presenting the target, but also the target to be viewed does not become fixed for the subject, so that it is perplexing. In contrast, in a case where the shift switch 44 is used, if the switch 34a is pressed while pressing the shift switch 44 in the state in which the vertical mask is applied, it is possible to instantly apply the horizontal mask over the upper stage. When the horizontal mask is to be applied over the lower stage, the changeover can be similarly effected by pressing the switch 34b while pressing the shift switch 44.

A description will be given of a case where the test is performed by using the one-character mask. To apply the one-character mask, the switch 34e is pressed. As a result, the one-character mask is applied over the right-end character in the upper stage of the presented target (chart). Each time the switch 34b is pressed in this state, the position of the one-character mask can be moved to the middle stage and to the lower stage in the right-end column, and by pressing the switch 34f the horizontal mask can be applied over the stage over which the one-character mask is positioned. When the measurement for one eye is finished, the eye to be measured is changed and measurement is effected. If the test is resumed with the same target character as that of the preceding test, the test result is liable to be inaccurate since the target characters are easy to remember; therefore, the masking position is generally changed. When the masking position is to be started from the left-hand end in the upper stage, if the operation is effected by the independent operation of the group of mask switches 34, the switch 34e is pressed to apply the one-character mask over the right-hand end in the upper stage, and then the masking position is consecutively changed in the leftward direction by the switch 34d. According to this procedure, not only does it take time in presenting the target, but also the target to be viewed does not become fixed for the subject. Hence, if the switch 34e is pressed while pressing the shift switch 44, it is possible to instantly apply the one-character mask over the right-hand end in the upper stage. In addition, the one-character mask can be applied over the left-hand end in the lower stage by means of the shift switch 44 and the switch 34d and over the right-hand end in the lower stage by means of the shift switch 44 and the switch 34c. The movement of the one-character mask can be effected by the switches 34a, 34b, 34c, and 34d.

Further, if the switch 34f is pressed while pressing the shift switch 44, the red-green filter can be applied over the target (chart) being currently presented. The red-green filter is used in the red-green test when a target having a higher visual acuity value or a lower visual acuity value than in the case of a red-green test with a predetermined visual acuity value is to used.

The unaided visual acuity test is performed by such masking, an unaided visual acuity value for the eye being measured is obtained by changing the presented target (chart) for masking, and that unaided visual acuity value is entered (when the one-character mask or the horizontal mask is applied, that visual acuity value is automatically entered).

<Testing of Spectacled Visual Acuity>

If the subject wears spectacles or the like, a spectacled visual acuity test is performed on the basis of the spectacle values. If the spectacle switch 38b of the group of measurement-mode designating switches 38 is pressed, the display screen of the display 30 is set in the spectacle measurement mode, and the spectacle value data which have been entered are invoked and displayed. In addition, since optical systems corresponding to the spectacle value data are disposed in the test windows 11 of the subjective-type refractive-power measuring device 2, the test can be conducted by disposing the lens units 10 in front of the subject's eyes. At this time, in a case where the spectacle value data have not yet been inputted, and the data are entered manually, if the input switch 39 is pressed as described before so as to use the numerical value input based on preset mode, the optical systems can be set instantly upon completion of the input without needing to operate the optical systems on each change of the input of numerical values.

In the spectacled visual acuity test, after a visual acuity test target (chart) is selected by means of the group of target switches 33, the presented target characters are changed by masking by using the group of mask switches 34 and the shift switch 44 in the same way as in the unaided visual acuity test, thereby obtaining visual acuity values for the eye to be measured, and the visual acuity values are inputted.

<Subjective Value Test>

After completion of the above-described preliminary test and input, the examination proceeds to the measurement of subjective values for determining binocular perfect correction powers. The subjective value measurement is effected by using the subjective-type refractive-power measuring device 2 and by executing the program B provided in the apparatus. First, a subjective switch 38d is pressed to set the mode in the subjective measurement mode, and the eye to be measured is designated by means of the switch 41. The objective value data copied onto the subjective value memory area are displayed in the central display portion 80 of the display 30. Optical systems corresponding to the objective value data are initially set in the test windows 11 of the lens units 10.

It should be noted that, depending on the examiner, the test in the subjective value measurement may be effected by an optical system based on the spectacle value data in accordance with his or her examination policy. In this case, after the spectacle value data are invoked on the central display portion 80 of the screen by pressing the spectacle switch 38b, the subjective switch 38d is pressed while pressing the shift switch 44, thereby making it possible to simply overwrite and copy the spectacle value data onto the subjective value memory area. The central display portion 80 is displayed in the subjective measurement mode, and optical systems corresponding to the spectacle value data are initially set in the test windows 11 of the lens units 10.

When the subjective measurement mode is set, the start switch 35 is pressed to start the selected program B. First, a test for confirmation of objective visual acuity is started for confirming the appropriateness of the objective value data (this test may be omitted when the spectacle value data have been initially set). A visual acuity test target (chart) having a combination of target characters having visual acuity values of 0.5 to 0.7 is presented in a masked state from the target presenting device 4. Since the test for confirmation of objective visual acuity in the prescription of spectacles is effected for the main purposes of confirmation of reliability of the objective value data and the presence of any abnormality in the visual function such as amblyopia in the eye being examined, a target having a minimum visual acuity value of 0.5, which is the standard in this confirmation, is initially presented in this apparatus. In the case of the eye being examined which cannot read the target having the visual acuity value of 0.5, a necessary measure is taken such as the reexamination of objective measurement or close examination.

As for the subsequent examination procedure of the optometric program B in this embodiment, a red-green (R/G) test conducted as a preliminary stage for the astigmatic test, an astigmatic-axis detection test, an astigmatic-power detection test, an R/G test for obtaining maximum visual acuity by preventing overcorrection, and a visual acuity test are carried out for one eye each, and a binocular balance test is subsequently effected to obtain binocular perfect correction powers. These tests can be consecutively advanced if the advance switch 36 is pressed, which in turn causes the microcomputer circuit 50 to issue an operation signal necessary for the test to the subjective-type refractive-power measuring device 2 and the target presenting device 4 (refer to Japanese Patent Application No. 192839/1996). Incidentally, in proceeding with this optometric program, when it has become necessary to return to the stage of an already-executed test, the operation can be returned to the state of an immediately preceding test stage by pressing the advance switch 36 while pressing the shift switch 44. Consequently, the reconducting or the like of the test is facilitated.

When binocular perfect correction powers have been obtained, the mode is set in the prescription mode by pressing the advance switch 36. The central display portion 80 of the screen is displayed in the prescription mode, and values of the perfect correction powers determined in the subjective value test are copied and displayed. In addition, the subjective values (perfect correction powers) are displayed in left and right display portions 81 (see FIG. 7). The examiner adjusts the determined perfect correction powers to prescription powers by taking into consideration of the subject's former spectacle powers, age, the purpose of use, and the like. Numerical values of S, C, and A are adjusted by changing the numerical values by turning the dial switch 42 clockwise or counterclockwise after designating each item by the group of switches 37 and designating the eye to be measured by the measurement-eye designating switch 41. The optical systems disposed in the test windows 11 of the lens units 10 are changed over by interlocking with the numerical-value adjustment by the dial switch 42. At this time, when the powers of S, C, and A are to be adjusted at one time, and the powers are to be adjusted by large degrees, the numerical-value input based on the aforementioned preset mode is used. That is, the input switch 39 is pressed to set the mode in the preset mode, and the numerical values of S, C, A and the like have been changed, only the numerical values displayed in the central display portion 80 can be changed without changing over the optical systems of the lens units 10. If the input switch 39 is subsequently pressed, the optical systems are instantly changed over to the optical systems corresponding to the inputted numerical values. As a result, it is possible to eliminate an uneasy sensation or discomfort imparted to the subject when the lenses are changed over in a ruffling manner in front of the subject's eyes, and it is possible to effect the examination accurately. In addition, if the dial switch 42 is operated while pressing the shift switch 44 as described above, an input can be made by changing the range of the adjustment step in correspondence with the item of adjustment.

It should be noted that if a plurality of candidates for prescription powers are to be made in the determination of prescription powers, the following procedure may be taken. After a first prescription power candidate has been determined, the objective switch 38c, for instance, is pressed while pressing the shift switch 44. Although the central display portion 80 is set in the objective value mode, data on the first prescription powers, which were previously displayed, are overwritten and copied onto the objective value memory area. By making use of this objective value memory area, data on a second prescription power candidate are made by changing the numerical values. Since optical systems corresponding to the data displayed in the central display portion 80 are disposed in the test windows 11 of the lens units 10, if a prescription switch 38e is pressed to invoke the first prescription power candidate again, it is possible to instantly change over the optical systems and allow the subject to make a comparison in the appearance. In addition, when a candidate for a prescription power is to be made further, respective memory areas are used by using the spectacle switch 38b and the subjective switch 38d with the shift switch 44.

In addition, this apparatus has automatic adjustment programs (refer to flowcharts of the automatic adjustment programs shown in FIGS. 9 to 14 as well as tables in FIG. 15 for obtaining correction amounts for adjusting correction powers) stored in the memory 51 for estimating prescription powers by adjusting correction powers with respect to the binocular perfect correction powers on the basis of adjustment factor information (former spectacle values, the accommodative power of the eye being examined, etc.). Hence, even an unskilled examiner is able to obtain rough estimates of appropriate prescription powers (since a detailed description thereof is given in Japanese Patent Application No. 192839/1996, the description thereof will be omitted). When the binocular perfect correction powers are determined and the mode is set in the prescription mode, this automatic adjustment program can be executed by pressing the prescription switch 38e while pressing the shift switch 44. The adjustment powers calculated by the automatic adjustment program are displayed in the central display portion 80 of the screen. The examiner makes fine adjustment of the calculated adjustment powers to determined prescription powers for far use.

Figure 16:
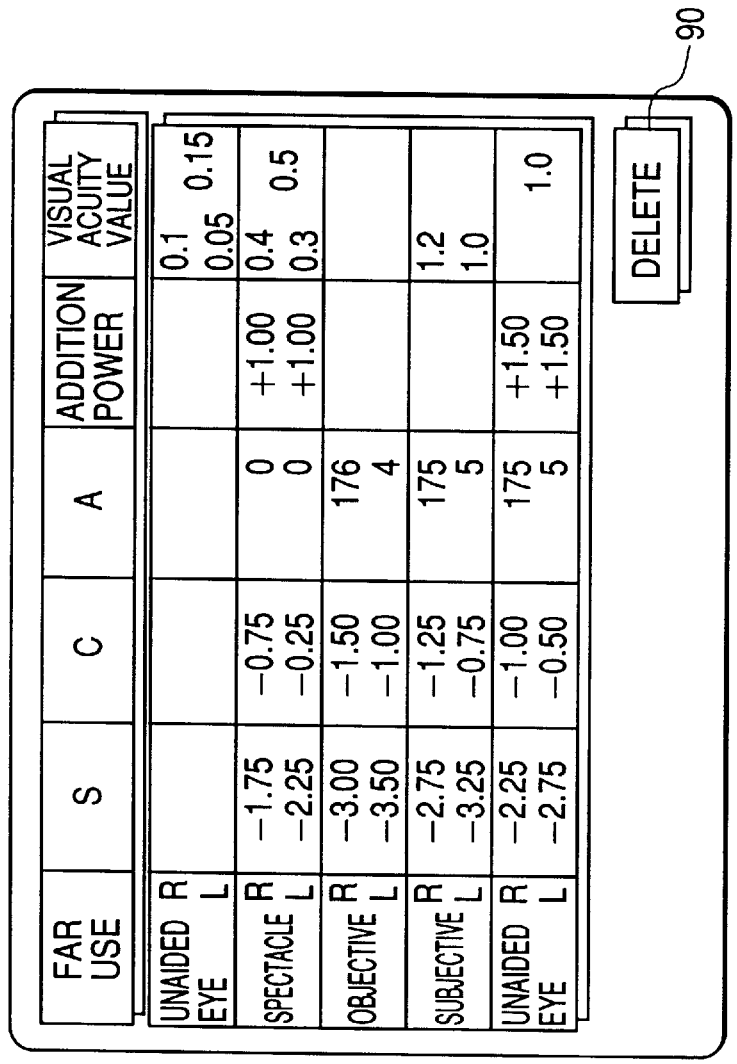
FIG. 16 is a diagram illustrating an example of display of a list of data on the test results which are displayed on the display.

After the prescription powers for far use are adjusted in the above-described manner, a test for near use is effected as required, and the prescription values based on the apparatus are determined. When all the tests are completed, and the test results are to be printed out, the print switch 40 is pressed. If a signal from the print switch 40 is entered only once, a list of data on the test results is displayed on the display 30, as shown in FIG. 16. Since this list of data is displayed before it is printed out from the printer 57, it is possible to confirm omissions in measurement or any abnormality in the data. If there has been an item or the like which remains unmeasured, it is possible to return to the final measurement screen by pressing the function switch 45 corresponding to a "DELETE" display 90 which is displayed at lower right of the screen. Since the test data in the controller 5 and the optical systems of the lens units 10 are not returned to the initial states, the test of the item which remains unmeasured can be effected easily. If the print switch 40 is pressed again after confirmation of the display of the list of data (as a result of the input of the signal from the print switch 40 in two successions), the test results are printed out from the printer 57.

In addition, this list of data is also displayed when the clear switch 47 is pressed, thereby allowing the examiner to confirm whether the data can be really deleted. Consequently, the deletion of data due to an erroneous operation and the like of the switch can be prevented, and the reconfirmation of the details of the test data can be prompted.

In the above-described manner, if the signal from the print switch 40 or the clear switch 47 is inputted only once, the list of data is displayed to allow the reconfirmation of the input. Only when the switch signal is inputted in two successions, the printing-out or the deletion can be executed. Whether or not this arrangement is to be used can be selected at the discretion of the examiner by the parameter setting.

What is claimed is:

1. An optometric apparatus having examining means for examining the visual function of an eye to be examined, comprising:

storing means for storing data on examination by said examining means;

display means having a display screen for displaying the examination data;

printing means for printing the examination data stored in said storing means;

a print switch for inputting a signal for printing the examination data to the printing means;

display control means for displaying the examination data on said display means on the basis of the signal from said print switch;

confirmation-signal generating means for generating a confirmation signal for confirming the absence of an abnormality in the examination data; and commanding means for commanding said printing means to effect printing on the basis of the confirmation signal.

2. An optometric apparatus according to claim 1, wherein said print switch is jointly used as said confirmation-signal generating means.

3. An optometric apparatus according to claim 1, further comprising:

examination-data deleting means for deleting the examination data on the basis of a print command signal from said commanding means.

4. An optometric apparatus according to claim 1, further comprising:

an examination-data deletion switch for generating a signal for deleting the examination data;

second display control means for displaying the examination data on said display means on the basis of the signal from said examination-data deletion switch;

second confirmation-signal generating means for generating a confirmation signal for confirming the absence of an abnormality in the examination data; and executing means for executing the deletion of the examination data on the basis of the confirmation signal.

5. An optometric apparatus according to claim 4, wherein said examination-data deletion switch is jointly used as said second confirmation-signal generating means.

6. An optometric apparatus according to claim 1, further comprising:

returning means for returning to a state of examination by said examining means.

7. An optometric apparatus according to claim 4, further comprising:

returning means for returning to a state of examination by said examining means.

* * * * *